(12) United States Patent
Volf

(10) Patent No.: US 12,415,084 B2
(45) Date of Patent: Sep. 16, 2025

(54) DEVICE FOR CARDIOLOGIC MAGNETIC AND OPTICAL STIMULATION

(71) Applicant: Imutec SAS, Paris (FR)

(72) Inventor: Nadia Volf, Paris (FR)

(73) Assignee: Imutec SAS, Paris (FR)

( * ) Notice: Subject to any disclaimer, the term of this patent is extended or adjusted under 35 U.S.C. 154(b) by 856 days.

(21) Appl. No.: 17/695,089

(22) Filed: Mar. 15, 2022

(65) Prior Publication Data

US 2023/0293900 A1 Sep. 21, 2023

(51) Int. Cl.
*A61N 2/00* (2006.01)
*A61N 2/02* (2006.01)
*A61N 5/06* (2006.01)

(52) U.S. Cl.
CPC ............. *A61N 2/002* (2013.01); *A61N 2/004* (2013.01); *A61N 2/02* (2013.01); *A61N 5/0613* (2013.01); *A61N 2005/0652* (2013.01); *A61N 2005/0659* (2013.01); *A61N 2005/0662* (2013.01)

(58) Field of Classification Search
CPC ........ A61B 5/0245; A61B 2018/00839; A61B 5/308; A61N 2005/0652; A61N 2005/0659; A61N 2005/0662; A61N 2/00; A61N 2/002; A61N 5/0601
USPC ........................................................... 600/13
See application file for complete search history.

(56) References Cited

U.S. PATENT DOCUMENTS

| | | | |
|---|---|---|---|
| 2005/0222625 A1 | 10/2005 | Laniado et al. | |
| 2006/0206174 A1* | 9/2006 | Honeycutt | A61N 2/02 600/27 |
| 2016/0271408 A1* | 9/2016 | Newton | A61N 1/3904 |
| 2018/0242875 A1* | 8/2018 | Volpe | A61B 5/0006 |
| 2020/0338348 A1 | 10/2020 | Honeycutt et al. | |
| 2021/0205574 A1 | 7/2021 | Garcia Molina et al. | |
| 2022/0200854 A1* | 6/2022 | Kane | H04L 41/0816 |

FOREIGN PATENT DOCUMENTS

| | | | | |
|---|---|---|---|---|
| CN | 101868280 A | * | 10/2010 | ......... A61N 1/36114 |
| EP | 1078649 A1 | * | 2/2001 | ........... A61N 1/3625 |
| ID | P202500635 A | * | 1/2025 | |
| JP | 7683871 B2 | * | 5/2025 | |
| WO | 9805379 | | 2/1998 | |

(Continued)

*Primary Examiner* — Brian L Casler
(74) *Attorney, Agent, or Firm* — Geoffrey Lottenberg; Berger Singerman LLP

(57) ABSTRACT

A system and method for determining and modifying the electromagnetic activity of a patient's heart includes a sensor array, a controller, software, and a stimulator array. The sensor array includes one or more sensors, such as an ECG electrode, that detect the electromagnetic activity of a patient's heart. The sensor array is in data communication with the controller. The controller runs software that outputs in human-format sensor data provided by the sensor array. The software receives data from the controller, analyzes the data, presents the data to the user, and sends the data to the stimulator array via a data communication link. The stimulator array includes one or more electromagnets and at least one or more light-emitting diodes. The stimulator array emits an electromagnetic (and/or light) field to modify the electromagnetic activity of a patient's heart based on the data it receives from the controller. The system can be portable.

18 Claims, 3 Drawing Sheets

(56) References Cited

FOREIGN PATENT DOCUMENTS

| WO | WO-2012048302 A2 * | 4/2012 | ........... A61B 5/4848 |
| WO | 2014/207407 A1 | 12/2014 | |
| WO | WO-2023079422 A1 * | 5/2023 | ............. A61B 5/358 |

* cited by examiner

DEVICE FOR CARDIOLOGIC MAGNETIC AND OPTICAL STIMULATION

FIELD OF INVENTION

The present invention generally relates to the real-time sensing and measurement of the electromagnetic field created by a patient's heart while synchronically creating and imposing an electromagnetic and/or optical field on the patient's body and on the area of the heart based on the real-time measured electromagnetic activity of the heart for the purpose of influencing the efficiency of biological processes and organ function.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts disclosed herein.

The accompanying drawings, which are incorporated in and constitute a part of the specification, illustrate embodiments of the disclosure and together with the general description of the disclosure given above and the detailed description of the drawings, given below, explain the principles of the disclosure.

In the drawings:

FIG. 1 is a schematic of the Electromagnetic Stimulation Device, in an embodiment.

FIG. 2 is a method flow chart of the invention, in an embodiment.

FIG. 3 is a graph of an ECG trace.

Figure 1:
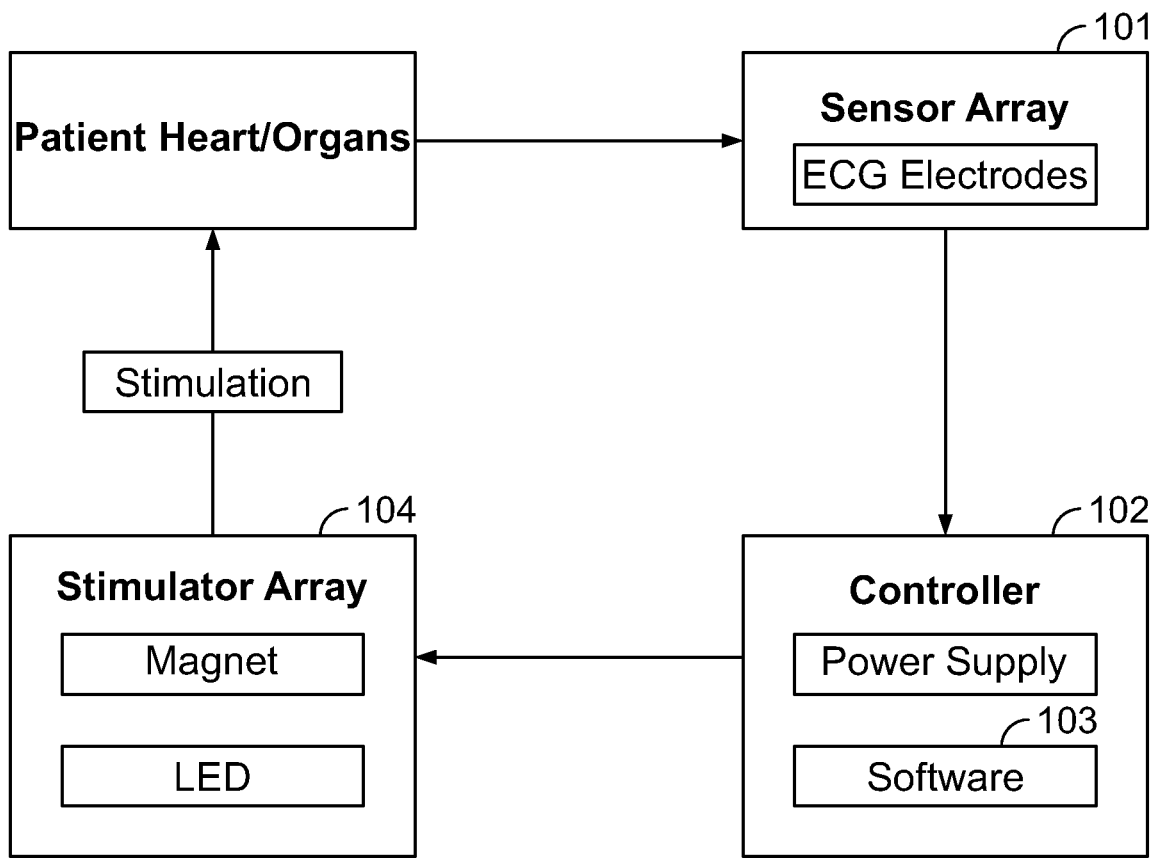
Figure 2:
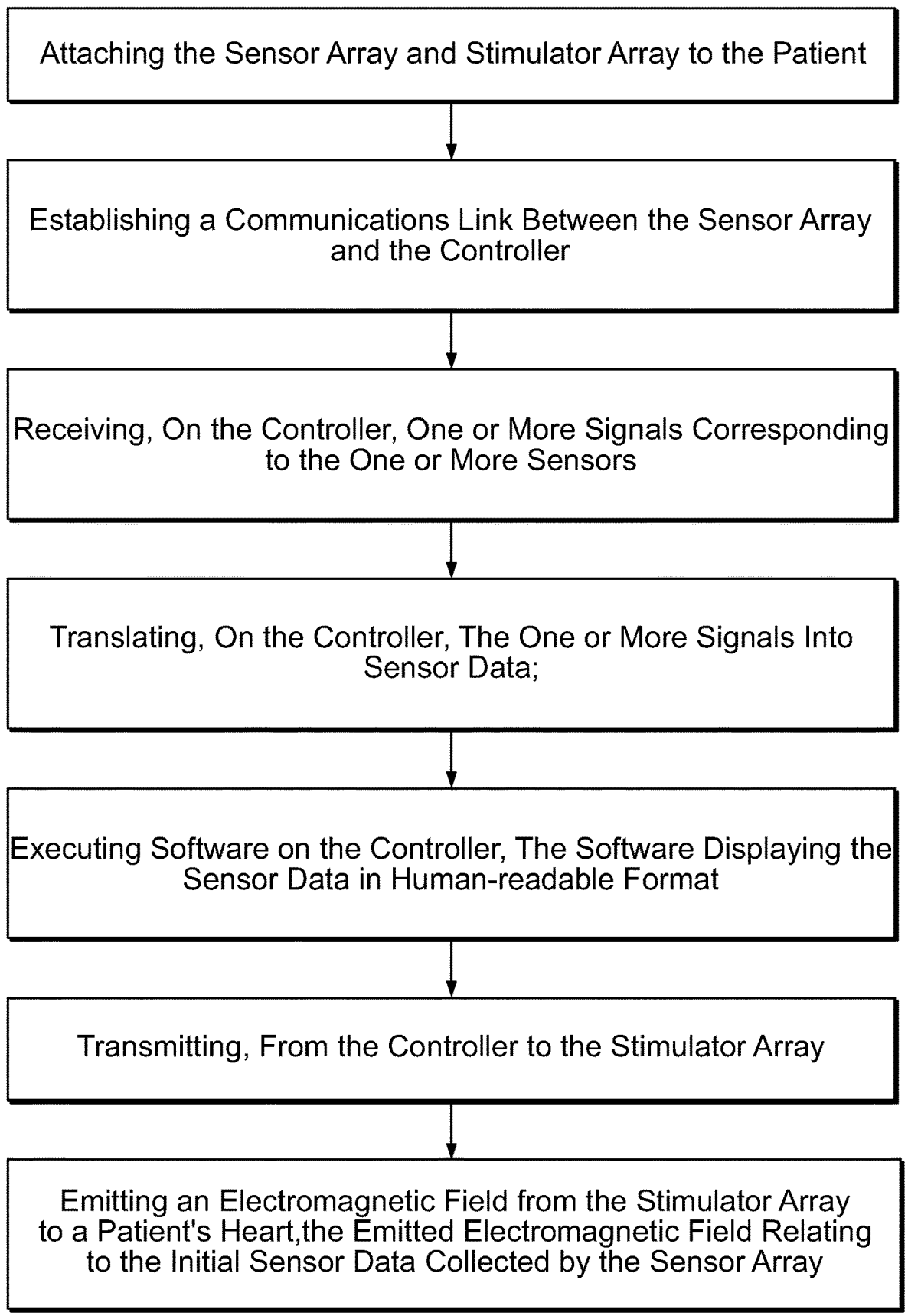

The drawings are not necessarily to scale. In certain instances, details that are not necessary for an understanding of the disclosure or that render other details difficult to perceive may have been omitted. It should be understood, of course, that the disclosure is not necessarily limited to the embodiments illustrated herein.

DETAILED DESCRIPTION

The present invention provides its benefits across a broad spectrum of endeavors. It is applicant's intent that this specification and the claims appended hereto be accorded a breadth in keeping with the scope and spirit of the invention being disclosed despite what might appear to be limiting language imposed by the requirements of referring to the specific examples disclosed. Thus, to acquaint persons skilled in the pertinent arts most closely related to the present invention, a preferred embodiment of the system is disclosed for the purpose of illustrating the nature of the invention. The exemplary method of installing, assembling and operating the system is described in detail according to the preferred embodiment, without attempting to describe all the various forms and modifications in which the invention might be embodied. As such, the embodiments described herein are illustrative, and as will become apparent to those skilled in the art, can be modified in numerous ways within the scope and spirit of the invention, the invention being measured by the appended claims and not by the details of the specification.

Although the following text sets forth a detailed description of numerous different embodiments, the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined herein, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, subparagraph (f).

Electromagnetic Stimulation Device Sensing, Measurement, and Output System

With reference to FIG. 1, the present invention contemplates an electromagnetic sensing, measuring, and output system. In some embodiments, the sensing, measuring, and output system is configured to non-invasively attach to a patient and comprises a sensor array 101, a controller 102, software 103, a stimulator array 104, and a power supply. In some embodiments, the sensor array 101 includes one or more sensors, including, for example, ECG electrodes.

In some embodiments, the sensor array 101 is configured to detect the electromagnetic activity of the patient's heart and send signals to the controller 102 via a data communication link. The controller 102 that is executing software 103 is configured to receive signals from the sensor array 101, translate the signals into digital readable data. The software 103 is configured to receive data from the controller 102, analyze that data, present the data visually to the user in human-readable format, and send the data to the stimulator 104 via a data collection link. In some embodiments the stimulator array 104 includes at least one or more electromagnets. In some embodiments the stimulator array 104 includes at least one or more light-emitting diodes. In some embodiments, the light-emitting diodes can emit light between visible and infrared light. In some embodiments, the electromagnets and light-emitting diodes of the stimulator array 104 emit an electromagnetic field (comprising, in some embodiments, light stimulation) that affects the electromagnetic activity of the patient's heart.

As noted, the sensor array 101 can comprise one or more sensors that are configured to detect the electromagnetic activity of a patient's heart. A controller 102 is used to transfer the sensor array data into readable data and translate that readable data to the software 103. A controller 102, for example a desktop computer, is used to execute the software 103. A software program 103 is used to visually present data to the user and, in some embodiments, send data to the stimulator array 104 via data communication link. The stimulator array 104 is used to create an electromagnetic field (including, in some embodiments, light stimulation) to modify the electromagnetic activity of the patient's heart. A data communication link can include, for example, ethernet, USB, PCI, Bluetooth, or wireless.

The invention also contemplates a portable version of the device in which the sensor array 101, controller 102, software 103, stimulator array 104, and the power supply all in an integrated housing. In some embodiments, the portable version of the invention is the size of a fist. A power supply can include, for example, an AC adaptor, a mains adaptor, a battery, or a rechargeable battery.

Electromagnetic Stimulation Device Sensing, Measurement, and Output Method

In some embodiments, the sensor array 101 continuously and in real-time monitors and captures the electromagnetic activity data of the patient's heart via at least one or more ECG electrodes. The sensor array 101 sends the electromagnetic activity data to a controller 102 and then the controller 102 feeds the data to software 103 that analyzes and records the measured electromagnetic data. This allows the user to analyze and detect electromagnetic activity of the patient's heart.

Once the device is activated, the sensor array 101 begins to measure the electromagnetic activity of the patient's heart. The electromagnetic activity measured by the sensor array 101 are sent to the controller 102 executing software 103 via a data communication link. The controller 102 converts the electromagnetic activity detected by the sensor array 101 and converts it into a digital form that can be read by software 103. The software 103 analyzes and displays the electromagnetic activity in a graph type report to the user. Based on the sensor data received from the controller 102, the stimulator array 104 emits an electromagnetic field that affects the electromagnetic activity of the patient's heart. In some embodiments, based on the graph form electromagnetic activity data the user is able to determine through observation how to proceed with the recharging process and/or whether the recharging process is complete.

In some embodiments, the data in the software 103 can be post-processed and the program can incorporate a feedback loop back to the stimulator array 104 to correct, modify, or enhance the electromagnetic activity of the patient's heart.

Figure 3:
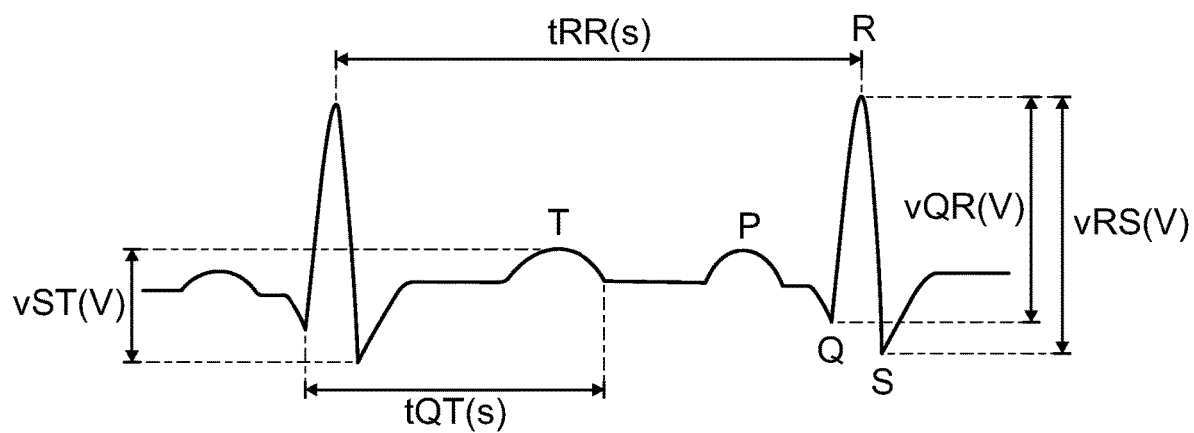

The controller 102 automatically and in real-time determines the value of the internal electrophysiological state of the heart and by extension the electromagnetic fields that are naturally created and transmitted throughout the patient, or the novel value Bion ($\beta$). Bion ($\beta$) represents the force momentum which is a measure of the average efficiency of all biochemical processes that take place in the heart. Bion ($\beta$), or force momentum, is calculated by dividing the summation of the amplitudes of QR+RS and ST waves (measured in mV), which represents the total global potential action, by the corrected time, tQTc. The corrected time tQTc avoids the influence of the variations of the heart rate modulated by breath, medications or pathological conditions. The equation defining this relationship may thus be expressed as shown below, where vQR is the charge potential, vRS is the discharge potential, and vST is the recharge potential and the corrected time tQTc is calculated by dividing the time tQT by the square root of the interval tRR, wherein tRR is the duration of an entire ECG cycle (identical points in an ECG recording). FIG. 3 is an ECG trace exemplifying the origin of these values, with the value $\beta$ calculated as follows:

$$\text{Force Momentum} = \frac{vQR + vRT + vST}{\frac{tQT}{\sqrt{tRR}}}$$

The value of force momentum $\beta$ in Bion dictates the electromagnetic field produced by the stimulator array 104.

Description of Computing Environment

Controller 102 can be connected to any external computing device smart phone, tablet computer, laptop computer, or other computing or mobile device capable of reading, and/or recording data about systems, devices, locations, and/or equipment, etc. Controller 102 can be connected to any external computing device, including any server computer, desktop computer, laptop computer, or other device capable of storing and managing data communication by and between one or more sensors of the sensor array 101 and the stimulation array 104.

In some embodiments, the controller 102 includes processing system, storage system, software, communication interface, and user interface. Processing system loads and executes software, including software 103, from storage system, including software module. When executed by controller 102, software module directs processing system to receive data, images, devices, locations, and/or equipment, etc. Such data could include any of the information described above, including but not limited to the functionality described herein. Additionally, controller 102 includes communication interface that can be further configured to transmit data to and receive data from controller 102.

The controller 102 includes a processing system that can comprise a microprocessor and other circuitry that retrieves and executes software from storage system. Processing system can be implemented within a single processing device but can also be distributed across multiple processing devices or sub-systems that cooperate in executing program instructions. Examples of processing system include general purpose central processing units, application specific processors, and logic devices, as well as any other type of processing device, combinations of processing devices, or variations thereof. Storage system can comprise any storage media readable by processing system, and capable of storing software. Storage system can include volatile and nonvolatile, removable and non-removable media implemented in any method or technology for storage of information, such as computer readable instructions, data structures, program modules, or other data. Storage system can be implemented as a single storage device but may also be implemented across multiple storage devices or sub-systems. Storage system can comprise additional elements capable of communicating with processing system.

An application interface can include data input and image display. In one example, data input can be used to collect information and data inputs from the user. It should be understood that although controller 102 is shown as one system, the system can comprise one or more systems to collect data.

Controller 102 includes processing system, storage system, software, and communication interface. Processing system loads and executes software from storage system, including software module 103. When executed by controller 102, software module 103 directs processing system to store and manage the data.

The processing system can comprise a microprocessor and other circuitry that retrieves and executes software from storage system. Processing system can be implemented within a single processing device but can also be distributed across multiple processing devices or sub-systems that cooperate in executing program instructions. Examples of processing system include general purpose central processing units, application specific processors, and logic devices, as well as any other type of processing device, combinations of processing devices, or variations thereof.

Storage system can comprise any storage media readable by processing system, and capable of storing software and data from the computing device. Data from computing device may be stored in a word, excel, or any other form of digital file. Storage system can include volatile and non-volatile, removable and non-removable media implemented in any method or technology for storage of information, such as computer readable instructions, data structures, program modules, or other data. Storage system can be implemented as a single storage device but may also be implemented across multiple storage devices or sub-systems. Storage system can comprise additional elements, such as a controller, capable of communicating with processing system.

Examples of storage media include random access memory, read only memory, magnetic disks, optical disks, flash memory, virtual memory, and non-virtual memory, magnetic cassettes, magnetic tape, magnetic disk storage or other magnetic storage devices, or any other medium which can be used to store the desired information and that may be accessed by an instruction execution system, as well as any combination or variation thereof, or any other type of storage media. In some implementations, the storage media can be a non-transitory storage media. In some implementations, at least a portion of the storage media may be transitory. In no case is the storage media a propagated signal.

In some examples, controller 102 can include a user interface. The user interface can include a mouse, a keyboard, a voice input device, a touch input device for receiving a gesture from a user, a motion input device for detecting non-touch gestures and other motions by a user, and other comparable input devices and associated processing elements capable of receiving user input from a user. Output devices such as a graphical display, speakers, printer, haptic devices, and other types of output devices may also be included in the user interface. The user input and output devices are well known in the art and need not be discussed at length here.

The included descriptions and figures depict specific implementations to teach those skilled in the art how to make and use the best mode. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., the use of a certain component described above alone or in conjunction with other components may comprise a system, while in other aspects the system may be the combination of all of the components described herein, and in different order than that employed for the purpose of communicating the novel aspects of the present disclosure. Other variations and modifications may be within the skill and knowledge of those in the art, after understanding the present disclosure. This method of disclosure is intended to obtain rights which include alternative embodiments to the extent permitted, including alternate, interchangeable and/or equivalent structures, functions, ranges or steps to those claimed, whether such alternate, interchangeable and/or equivalent structures, functions, ranges or steps are disclosed herein, and without intending to publicly dedicate any patentable subject matter.

What is claimed is:

1. A method of determining and modifying the electromagnetic field of a patient's heart, comprising:
providing a sensor array, a controller, software, and a stimulator array wherein the sensor array comprises one or more sensors configured to detect the electromagnetic field of a patient's heart;
establishing a communications link between the sensor array and the controller;
receiving, by the controller, one or more signals corresponding to the one or more sensors;
translating, with the controller, the one or more signals into sensor data;
executing software on the controller, the software displaying the sensor data in human-readable format, the sensor data corresponding to the electromagnetic field of a patient's heart;
wherein the controller calculates a force momentum of the heart, value β, according to the formula:

$$\text{Force Momentum} = \frac{vQR + vRT + vST}{\frac{tQT}{\sqrt{tRR}}}$$

transmitting, from the controller to the stimulator array, the sensor data;
emitting an electromagnetic field from the stimulator array to a patient's heart, the emitted electromagnetic field relating to the sensor data collected by the sensor array.

2. The method of claim 1, wherein the sensors include one or more ECG electrodes.

3. The method of claim 1, wherein the stimulator array includes at least one more or electromagnets.

4. The method of claim 1, wherein the stimulator array includes at least one or more light-emitting diodes.

5. The method of claim 4, wherein the light-emitting diodes emit light between visible and infrared light.

6. The method of claim 1, further comprising the step of establishing a communications link between the controller and the stimulator array, and, via the software, sending feedback signals from the controller to the stimulator array to modify the electromagnetic activity of a patient's heart.

7. The method of claim 1, wherein the software is enabled for post-processing of sensor data.

8. The method of claim 1, wherein a condition of an electromagnetic field of a patient's heart as determined by the one or more sensors is readable via one or more output graphs.

9. The method of claim 1, wherein the emitted electromagnetic field from the stimulator array affects the electromagnetic activity of a patient's heart.

10. The method of claim 1, wherein the value of the force momentum dictates the electromagnetic field emitted by the stimulator array.

11. A system of determining and modifying the electromagnetic activity of a patient's heart, comprising:
a sensor array, a controller, software, a stimulator array, and a power supply;
the sensor array comprising one or more sensors configured to detect the electromagnetic activity of a patient's heart;
the sensor array in communication with the controller, the controller configured to translate signals received from the one or more sensors and translate the signals into sensor data; and
the controller executing software, the software configured to output the sensor data received from the controller to enable a user to read the electromagnetic activity of a patient's heart by the one or more sensors; and
wherein the controller calculates a force momentum of the heart, value β, according to the formula:

$$\text{Force Momentum} = \frac{vQR + vRS + vST}{\frac{tQT}{\sqrt{tRR}}}.$$

12. The system of claim 11, wherein the sensors include at least one or more ECG electrodes.

13. The system of claim 11, wherein the stimulator array includes at least one or more electromagnets.

14. The system of claim 11, wherein the stimulator array includes at least one or more light-emitting diodes.

15. The system of claim 11, wherein the controller is configured to be in communication with the sensor array to send feedback signals to the stimulator array to modify the electromagnetic activity of a patient's heart.

16. The system of claim 11, wherein the electromagnetic conditions of a patient's heart as determined by the one or more sensors is readable via one or more output graphs.

17. The system of claim 11, wherein the stimulator array emits an electromagnetic field that affects the electromagnetic activity of a patient's heart, wherein the value of the emitted electromagnetic field is dictated by the value of the force momentum.

18. The system of claim 11, wherein the sensor array, controller, software, stimulator array, and power supply are in a singular integrated, portable housing.

* * * * *